(12) United States Patent
DuBourdieu et al.

(10) Patent No.: US 8,501,220 B2
(45) Date of Patent: Aug. 6, 2013

(54) STABILIZED LIQUID EGG MATERIAL FOR EXTENDED SHELF LIFE

(75) Inventors: Daniel J. DuBourdieu, Limerick, ME (US); Rajiv Lall, Menomonie, WI (US)

(73) Assignee: R&D Lifesciences, Menomonie, WI (US)

( * ) Notice: Subject to any disclaimer, the term of this patent is extended or adjusted under 35 U.S.C. 154(b) by 148 days.

(21) Appl. No.: 12/980,536

(22) Filed: Dec. 29, 2010

(65) Prior Publication Data

US 2011/0159002 A1    Jun. 30, 2011

Related U.S. Application Data

(60) Provisional application No. 61/291,675, filed on Dec. 31, 2009.

(51) Int. Cl.
*A61K 47/00* (2006.01)
*A61K 39/00* (2006.01)

(52) U.S. Cl.
USPC ........................................................ 424/439

(58) Field of Classification Search
None
See application file for complete search history.

(56) References Cited

U.S. PATENT DOCUMENTS

| | | | |
|---|---|---|---|
| 4,882,194 A | 11/1989 | Rapp | |
| 5,431,939 A | 7/1995 | Cox et al. | |
| 6,056,984 A | 5/2000 | Ekanayake et al. | |
| 6,086,878 A | 7/2000 | Adalsteinsson et al. | |
| 6,403,141 B1 | 6/2002 | Liot | |
| 7,211,287 B2 | 5/2007 | Efstathiou et al. | |
| 7,256,270 B2 | 8/2007 | Nash et al. | |
| 7,534,433 B2 | 5/2009 | Pimentel | |
| 7,579,002 B2 | 8/2009 | Cook et al. | |
| 2006/0182730 A1 * | 8/2006 | Kodama et al. | 424/94.3 |

OTHER PUBLICATIONS

Chang, H.M. et al., Productivity and some properties of immunoglobulin specific against *Streptococcus* mutans serotype C in chicken egg yolk (IgY). *J Agric. Food Chem*, (1999), 47:61-66.

Hatta, H. et al., Passive immunization against dental plaque formation in humans: effect of mouth rinse containing egg yolk antibodies (IgY) specific to *Streptococcus mutans.*, *Caries Res.*, (1997), 31:268-274.

Kassaify, Z.G. et al., Identification of antiadhesive fraction(s) in non-immunized egg yolk powder: *in vitro* study. *J Agric. Food Chem.*, (2005), 53:4607-4614.

Quigley, J.D. et al., Addition of Soybean Trypsin Inhibitor to Bovine Colostrum: Effects on Serum Immunoglobulin Concentrations in Jersey Calves. J. Dairy Sci (1995), 78:886-892.

Sugita-Konishi Y. et al., Inhibition of bacterial adhesion and Salmonella infection in BALB/c mice by siayoligosaccharides and their derivatives from chicken egg yolk. *J. Agric. Food Chem.*, (2002), 50:36073613.

* cited by examiner

*Primary Examiner* — Brian J Gangle
(74) *Attorney, Agent, or Firm* — Charles S. Sara, Esq.; Daniel A. Blasiole; DeWitt Ross & Stevens, S.C.

(57) ABSTRACT

The present invention is directed to shelf-stable liquid egg material, methods for making the same, and method of using the same. The present invention is also directed to an animal feed supplement containing a stabilized IgY antibody titer in liquid eggs stored at room temperature for extended periods of time with the use of glycerol and preservatives. The stabilized liquid whole egg or stabilized liquid yolks of the egg containing non-specific or elevated specific IgY titer may be used as animal feed supplements animals to provide passive immunity to these animals. The stabilized nature of the IgY and liquid egg allows for extended shelf life of these liquid products at room temperature.

25 Claims, No Drawings

STABILIZED LIQUID EGG MATERIAL FOR EXTENDED SHELF LIFE

CROSS-REFERENCE TO RELATED APPLICATIONS

This application claims priority under 35 USC §119(e) to U.S. Provisional Patent Application 61/291,675 filed Dec. 31, 2009, the entirety of which is incorporated herein by reference.

BIBLIOGRAPHY

Complete bibliographical citations to the documents cited herein can be found in the Bibliography immediately preceding the claims.

FIELD OF THE INVENTION

The present invention relates to shelf-stable liquid egg products comprising IgY antibodies. The liquid egg products are formulated to retain IgY titer and activity while being stored at room temperature in a liquefied state. The present invention also relates to animal feed supplements comprising the shelf-stable liquid egg products. In particular, the present invention relates to a stabilizing composition for adding to a whole egg or egg yolk. The composition components complex with IgY to maintain IgY titer and activity for storage at extended periods of time.

BACKGROUND

IgY derived from hyperimmunized chicken eggs has been added as a supplement to animal feed to provide passive immunity in other animals. By a process of vaccination, chickens or other egg-laying animals can be immunized against specific microorganisms and other antigens. Increased titers of antibodies can be obtained by a process of hyperimmunization. Hyperimmunization procedures are well-known in the art and have been described in detail. High amounts of specific antibodies can be obtained by immunizing animals with specific antigens and isolating the antibodies from the egg yolk, milk, colostrum or serum. While it has been known since 1893 that the IgY antibody is found in the yolks of chicken eggs (Klempeler 1893), it is only in the last 20 years or so that use of IgY has gained ground as a practical source of passive immunity in livestock or other animals. While nature intended liquid colostrum as the source of antibodies to provide the initial passive immunity that a newborn animal receives from its mother, in the modern agriculture industrial practice it has become necessary to provide passive immunity from various antibody supplements in order to achieve profitability.

The supplements that the animal feed industry uses to provide passive immunity to animals have been derived from colostrum, blood serum and, more recently, from chicken egg IgY antibodies. The use of IgY antibodies to provide passive immunity provides certain advantages over the use of antibodies found in colostrum or antibodies found in blood serum. These advantages include the relative cost efficiency to create specifically directed antibodies against pathogenic organisms compared to colostrum or blood serum antibodies.

Passive immunity is the transfer of active humoral immunity in the form of ready-made antibodies, from one individual to another. Passive immunity can occur naturally, when maternal antibodies are transferred to the offspring. It can also be induced artificially, when high levels of antibodies specific for a pathogen or a toxin are recovered from immunized individuals and administered to non-immune individuals. The antibodies' transfer may be carried out via systemic, intravenous or oral routes. The oral route is the route of choice for localized treatment of digestive tract infections. Immunity derived from passive immunization lasts for only a short period of time, i.e., for as long as the antibodies remain in the organism, but it provides immediate protection.

In animals, the administration of preformed, specific antibodies is an attractive approach to establish protective immunity against viral and bacterial pathogens. It is becoming a more interesting alternative to control the increasing number of antibiotic-resistant organisms. Passive immunization can also be used against organisms that are non-responsive to antibiotic therapy.

Antigen-specific IgY antibody can be produced on a large-scale from eggs laid by chickens immunized with selected antigens (Hatta et al., 1997). The laying hen transfers all antibody isotypes found in the chicken to the egg, i.e., IgY, IgM, and IgA antibodies. The yolk contains only IgY, while IgM and IgA are found only in the white. The chicken's serum IgY level is reflected in the egg yolk shortly after a single administration of antibody, about one week. Egg yolk contains approximately 3-25 mg IgY/ml. Depending on its weight, therefore, each egg could provide 40-500 mg IgY.

The use of IgY for passive immunization has been studied extensively, demonstrating its effectiveness in preventing or treating infectious diseases caused by various pathogens in animal models, especially those of the gastrointestinal (GI) tract. Antibodies are usually administered in the feed in several forms: whole egg powder, whole yolk powder, water-soluble fraction powder or purified IgY material. The powdered egg formats containing IgY or other anti-bacterial components are typically packaged into containers or made into pastes. The powders are mixed into dry feed and subsequently given to the animal. The pastes are squirted into the mouth of the animal.

The animal feed industry also uses liquid feed supplements as a standard method of providing supplements to animals, due to cost considerations and ease of use considerations. A liquid format is desirable since it is easy to administer liquids in drenches or even in watering systems. However, a stabilized liquid format that maintains titers of IgY derived from hyperimmunized chicken eggs for an extended shelf life has not been developed.

The methods that are currently used to preserve IgY titer from eggs involve either expensive spray-drying or freeze-drying techniques for the whole egg or egg yolk and converting the egg into a powder. However, both of these methods have problems in maintaining the original structure of the IgY and binding activity of the IgY molecule. Spray-drying methods use heat during the processing of the egg material that will denature the IgY molecule to a large extent. IgY denatures when thermally treated at temperatures higher than 75° C. (Chang et al., 1999). Freeze-drying methods involve freezing the egg material which also can structurally alter the IgY molecule. Chansarkar (1998) showed that frozen or freeze-dried IgY resulted in loss of antigen-binding activity and a significant drop in the solubility under the conditions of high salt and protein concentrations.

Keeping the IgY antibody in a liquid state from the time it is in the egg to the time it is used is the best method to maintain the structure of the IgY molecule, to prevent degradation, and preserve its binding activity in providing passive immunity. Keeping the hyperimmune eggs in their egg shell without cracking them open is not a practical commercial method. Whole eggs stored at room temperature will naturally start degrading within several weeks and are also not practical to use as a delivery means to the animal.

Keeping whole egg or yolk products in a stable liquid state at room temperature without degradation of the liquid matrix or the IgY content for periods of time greater than few hours or even a day is a problem to the animal feed industry. This is due to oxidation issues, contamination issues, and coagulation issues of liquid egg products. Attempts at keeping whole eggs or liquid yolks as a stabilized liquid matrix have been the subject of a number of patents for human products. These methods principally involve pasteurization of the egg product at various temperatures. For example, U.S. Pat. No. 6,403,141 is directed to a method of obtaining a long shelf life for liquid egg products using pasteurization techniques. This method allows storage of whole egg products at room temperature for 3 months without the incorporation of additives. However, this patent has not addressed the overriding issue of IgY stability when storing the products at room temperature and use a different technology approach than the current invention to extending shelf life of the matrix.

Other methods of purifying IgY on a commercial scale may lose important factors that may be involved in the efficacy of whole chicken eggs or whole yolks when providing antibacterial properties. While IgY is the focus of passive immunity, it has also has been shown that anti-bacterial properties were associated with egg yolk components other than the IgY. Among these components are the granule high-density lipoprotein (HDL) (Kassaify et al., 2005), the plasma low-density lipoprotein (LDL) (Brady et al., 2002), and the egg-yolk-derived sialyloligosaccharide (YDS) (Sugita-Konish et al., 2002). As such, it desirable to maintain these components when providing passive immunity in a liquid egg product by making sure the entire yolk is used or the entire contents of the egg are used and not using just purified IgY.

SUMMARY OF THE INVENTION

It is an object of this invention to increase the shelf life of one or more antibodies, including IgY, obtained from the egg of an egg-producing animal that has been immunized against one or more immunogens, when kept in a liquid state. In particular, the invention is directed to increasing the stability and maintaining activity of the IgY in a liquid egg material.

In one broad aspect, the present invention is directed to a shelf-stable liquid egg material. The shelf-stable liquid egg material comprises a liquid egg material enriched with an antibody at a hyperimmunized titer, in addition to additional ingredients selected from the group consisting of an antibody protectant, an antioxidant, an antimicrobial agent, an enzyme inhibitor, and an alkalinizing agent. The additional ingredients are present in concentrations effective to extend shelf life of the liquid egg material and/or the antibody contained therein.

In another broad aspect, the invention is directed to a method of making a shelf-stable liquid egg material as described herein. The method comprises inducing an immune response in an egg-producing animal with at least one antigen to produce an antibody at a hyperimmunized titer; collecting an egg from the egg-producing animal following induction of the immune response; processing inner content of the egg to obtain a liquid egg material; and adding to the liquid egg material an antibody protectant, an antioxidant, an antimicrobial agent, an enzyme inhibitor, and an alkalinizing agent in concentrations effective to extend shelf life of the liquid egg material.

In yet another broad aspect, the invention is directed to a method of using a shelf-stable liquid egg material as described herein. The method comprises administering the liquid egg material to an animal to provide passive immunity to the animal.

The present invention provides a method of maintaining the IgY titer and maintaining the liquid egg matrix at room temperature for an extended shelf life without having to use expensive and sometimes detrimental spray-drying or freeze-drying techniques. These advantages are important when commercializing an IgY product as a liquid animal feed supplement.

Advantageously, the processed liquid egg material of the present invention may be stored in a stabilized blend at room temperature for at least 6 months to a year, 1 to 2 years when kept refrigerated, and greater than 2 years when kept frozen, and still maintain the binding activity of the antibody and matrix stability of the liquid egg material.

The objects and advantages of the invention will appear more fully from the following detailed description of the preferred embodiment of the invention.

DETAILED DESCRIPTION OF THE INVENTION

Definitions

Unless otherwise noted, the following definitions will apply to the terms throughout this disclosure:

"Antimicrobial preservatives and agents" mean agents that kill microbes, i.e., biocidal agents, and agents that retard microbe growth, i.e., static agents. As used here, "microbes" means bacteria, fungi, viruses, prions, protozoa or any other microscopic organism capable of spoiling food.

"Content" or "contents" of an egg refers to any portion of the egg, in whole or in part. In a preferred version of the invention, the content of an egg comprises the inner content of the egg. "Inner content" of an egg refers to any portion of the egg, in whole or in part, minus the shell, and includes the egg whites and/or the egg yolks.

"Egg-producing animal" refers to any egg-producing or egg-laying animal capable of producing antibodies to an antigen and passing along the antibodies in its eggs. Avian egg-producing animals are preferred. Non-limiting examples of suitable avian egg-producing animals include chickens, turkeys, ducks, and ostriches.

"Processing" inner content of an egg refers to any method of obtaining and blending the inner content of the egg into a relatively homogeneous, liquid form. Such processing includes, without limitation, cracking the egg to obtain the inner content, and blending the inner content using methods known in the art. If inner content from more than one egg is extracted, then the total collected inner content may be processed to form a blend of liquid egg material.

"Hyperimmunization" is the process of repeated injections of an antigen leading to high levels of an antibody in a body.

"Hyperimmunized titer" refers to a level of an antibody against an antigen in an animal as would result from hyperimmunization of the animal with the antigen.

"IgY and other antibodies" refers to the classes of immunoglobulins found in chickens or other avian egg-producing animals and comprises IgY, IgA and IgM.

"Induction of an immune response" refers to any process of stimulating production of antibodies, preferably against a specific antigen or antigens, in an animal. Methods include any known or developed methods of vaccination or immunization. In a preferred version, induction of an immune response comprises injecting the particular antigen or antigens in an animal, which causes the animal to produce an antibody against the antigen or antigens. "Immunogen is used herein interchangeably with "antigen."

"Liquid egg material" refers to inner content of an egg that has been extracted from the egg and, if necessary, processed into liquid form. Liquid egg material may include the yolk, egg whites, and/or any other additives or ingredients described herein.

"Liquid whole egg" means a liquid egg material comprising liquid egg white and liquid egg yolk.

"Liquid egg yolk" means liquid egg yolk that is substantially free of liquid egg white. Liquid egg yolk can be obtained by separating the yolk from egg white and processing the egg yolk into liquid form.

"Liquid egg white" means liquid egg white substantially free of egg yolk or liquid egg yolk. Liquid egg white may be obtained by separating the egg white from the egg yolk. Processing of the egg white may be required.

Described in this disclosure is a method for extending the shelf life of liquid egg material, without the need of heat treatment. The shelf-stable liquid egg material comprises the inner content of eggs (whole egg, egg yolk, and/or egg whites) in combination with additional ingredients such as protectants, antioxidants, and preservatives. The additional ingredients are added to stabilize the IgY and other antibodies within the liquid egg material to ensure an extended shelf life when stored at room temperature, refrigerated or frozen. The stabilized IgY in the egg is then used to provide passive immunity in another animal. At least some of the ingredients additionally enhance the efficacy of the liquid egg material in the animal.

It is well known that antibody produced in one species can be used to neutralize the effects of the corresponding antigen in other species. Passive immunization occurs when an individual receives immune protection from antibodies produced in another individual. These individuals can be of the same species or from different species. For example, chicken hens may be immunized with a vaccine for calf scours in order to obtain high amounts of specific antibodies against pathogenic *E. coli* strains that cause scours in calves. The antibody-containing yolk obtained from an egg of the immunized hen will have activity against such *E. coli* strains. If administered to calves, the antibody-containing yolk is effective in protecting calves from attack by the scours-causing bacteria.

One specific version of the present invention is directed to a method for increasing the stability of the IgY in a liquid egg material to form a stabilized blend of liquid egg material and administering the stabilized blend of liquid egg material to an animal, comprising:

A. inducing an immune response in an egg-producing animal with at least one immunogen;

B. collecting eggs from the egg-producing animal for a predetermined period of time following induction of the immune response;

C. processing all of the collected eggs together to form a blend of liquid whole egg material or liquid yolk material;

D. adding a protectant to stabilize and maintain the structural integrity of the antibody and the integrity of the other contents of the blend;

E. adding antioxidants to the blend;

F. adding antimicrobial preservatives to the blend;

G. adding digestive enzyme inhibitors to the blend;

H. adding alkalinizing agents to the blend;

I. storing the stabilized blend in suitable containers for an extended shelf life; and J. administering to the stabilized blend to an animal to provide passive immunity.

Liquid Egg Material:

The present invention includes a liquid egg material prepared from whole eggs, yolks of eggs, and/or egg whites. The liquid egg material preferably contains IgY and/or other antibodies, preferably at least IgY antibodies, from hyperimmunized chickens or other egg-producing animals. The liquid egg material may include content derived from whole eggs, egg yolks, or egg whites, provided that the liquid egg material contains IgY or other antibodies from the immunized animals. Preferably, the liquid egg material includes content derived from egg yolks.

Eggs are collected from the egg-producing animal after immunization. The eggs are preferably collected for a predetermined period of time after immunization wherein the IgY titers in the eggs are the highest. This predetermined period of time can be determined by testing the IgY tiers by ELISA or other methods known in the art. The resultant IgY antibody-containing eggs are cracked open to obtain the entire liquid content inside them. Preferably, the whole-egg liquid content is additionally separated to obtain just the yolk, where IgY antibodies are predominantly found.

Antibody Protectants

The IgY is stabilized by adding antibody protectants. Non-limiting examples of such antibody protectants include glycerol, propylene glycol, ethylene glycol, or combinations thereof. These protectants serve to maintain the antibody structure. The protectants also serve to maintain the liquid egg material matrix and thus act as stabilizers. Along with water, the protectants act to promote softness and flexibility of the liquid egg material. This prevents drying out of proteins such as IgY or other compounds found in the egg matrix. Preservation of the IgY structure and activity is maintained by preventing such drying.

The antibody protectants can be added to the liquid egg product in any effective concentration to extend the shelf life of the liquid egg product. For example, the range of protectants added to the liquid egg material can be from about 1% to 60% v/v, preferably from about 10% to 40% v/v, and more preferably from about 15% to about 30% v/v.

The preferred antibody protectant is glycerol in an amount of about 20% v/v.

Antimicrobial Agents:

Antimicrobial agents are added to the liquid egg material to prevent the growth of bacteria, viruses, molds or fungus during long term storage. The antimicrobial agents added to the liquid egg material are preferably food grade material, i.e., capable of being ingested by an animal without causing deleterious health effects.

Non-limiting examples of antimicrobial agents include sugars such as sucrose or salts such as sodium chloride, which work through osmotic means to destroy bacteria. Other antimicrobial agents such as potassium sorbate, methylparaben or propylparaben can inhibit the growth of fungus and molds. Natural anti-bacterial agents, such as essential oils, can be added to prevent bacterial contamination. Examples of suitable essential oils include oregano, garlic, thyme, rosewood, celery seed, frankincense, yiang yiang, cedarwood, lime, orange, petitgrain, bergamot, lemon, grapefruit, mandarin, myrrh, coriander, pumpkin, cypress, lemongrass, palmarosa, citronella, carrot seed, eucalyptus, fennel, wintergreen, juniper, French lavender, Tasmanian lavender, macadamia, tea tree, cajuput, niaouli, peppermint, spearmint, basil, evening primrose, marjoram, geranium, aniseed, bay, pine, black pepper, patchouli, apricot kernel, sweet almond, rosemary, sage, clary sage, sandalwood, clove, vetiver, and ginger oils.

The antimicrobial agents can be added to the liquid egg product in any effective concentration to extend the shelf life of the liquid egg product.

For example, suitable concentrations of sucrose range from about 1% w/v to 60% w/v, preferably from about 5% w/v to about 30% w/v and most preferably from about 10% w/v to about 15% w/v.

Suitable concentrations of sodium chloride range from about 1% w/v to 30% w/v, preferably from about 5% w/v to about 20% w/v and most preferably about 10% w/v.

Suitable concentrations of potassium sorbate range from about 0.01% w/v to 0.1% w/v, and preferably about 0.1% w/v.

Suitable concentrations of propylparaben and methylparaben range from about 0.01% w/v to 0.1% w/v, preferably from about 0.05% w/v to about 0.1% w/v and most preferably from about 0.08% w/v to about 0.1% w/v.

Suitable concentrations of essential oils range from about 0.0001% v/v to 5% v/v, preferably from about 0.1% v/v to about 2% v/v and most preferably from about 0.5% v/v to about 1% v/v.

Antioxidants:

Antioxidants are added to the liquid egg material to prevent oxidation and degradation of IgY, other antibodies, and other components of the liquid egg material. Examples of suitable antioxidants include tocopherol, gallic acid ester, dibutyl hydroxy toluene (BHT), butyl hydroxy anisol (BHA), ascorbic acid (vitamin C), vitamin E, and combinations thereof.

The antioxidants can be added to the liquid egg product in any effective concentration to extend the shelf life of the liquid egg product.

Suitable concentrations of vitamin E and vitamin C range from about 0.01% w/v to about 5% w/v, and preferably about 0.1% w/v.

Suitable concentrations of dibutyl hydroxyl toluene (BHT) and butyl hydroxyl anisol (BHA) range from about 0.01% w/v to about 0.02% w/v, preferably from about 0.015% w/v to about 0.018% w/v and most preferably from about 0.016% w/v to about 0.017% w/v.

Digestive Enzyme Inhibitors:

The preferred method of administering the liquid egg material of the present invention to an animal is through oral administration by including it as a feed supplement. For the IgY feed supplement to be optimally effective, the IgY should survive passage through the stomach and reach the gastrointestinal tract. The stomach of an animal contains enzymes and acids that help digest food, which would potentially damage the IgYs in the administered liquid egg material.

Digestive enzyme inhibitors are added to the liquid egg material to prevent digestion of the IgY in the stomach of the animal in which the liquid egg material is orally administered. Examples of suitable digestive enzyme inhibitors include soybean trypsin inhibitor, a chymotrypsin inhibitor, a carboxypeptidase inhibitor, a papain inhibitor, a pepsin inhibitor, and other protease or peptidase inhibitors. Preferably, the digestive enzyme inhibitor is soybean trypsin inhibitor. Trypsin inhibitors inhibit the absorption of proteins by reducing the activity of the enzyme trypsin, which is necessary for degrading proteins to amino acids. This allows the IgY antibody to pass through the stomach of the animal and into the gastrointestinal tract. Once the IgYs are in the gastrointestinal tract, they can interact with specific pathogens in the gastrointestinal tract, such as *E. coli*, and provide passive immunity to the animal.

Additionally, the digestive enzyme inhibitors help protect against native protease or peptidase enzymes in the liquid egg material.

The digestive enzyme inhibitors can be added to the liquid egg product in any effective concentration to extend the shelf life of the liquid egg product and/or to provide passive immunity to an animal to which the liquid egg material is administered.

Suitable concentrations of the digestive enzyme inhibitors range from about 0.0001% w/v to about 0.1% w/v, preferably from about 0.001% w/v to about 0.05% w/v and most preferably from about 0.03% w/v to about 0.04% w/v.

Alkalinizing Agents:

Alkalinizing agents are added to the liquid egg material to prevent acid-dependent denaturization of IgYs in the stomach of an animal to which the liquid egg material is administered. Alkalinizing agents can include sodium carbonate, sodium bicarbonate, calcium carbonate, magnesium carbonate or combinations thereof. Alkalinizing agents raise the pH of the stomach by interacting with stomach acids and neutralizing them. This allows the IgY antibodies to be protected when passing through the animal stomach to the gastrointestinal tract to provide passive immunity to the animal. The alkalinizing agents also maintain the pH of the liquid egg material while in storage to extend its shelf life.

The alkalinizing agents can be added to the liquid egg product in any effective concentration to extend the shelf life of the liquid egg product and/or to provide passive immunity to an animal to which the liquid egg material is administered.

Suitable concentrations of alkalinizing agents range from about 2.0% w/v to about 10% w/v, preferably from about 3% w/v to about 8% w/v and most preferably from about 4% w/v to about 6% w/v.

Preferred Concentrations:

A preferred formula for the liquid egg material includes the following recipe:
- 10% w/v sodium chloride;
- 20% v/v glycerol;
- 0.1% w/v potassium sorbate;
- 0.1% w/v vitamin E;
- 0.1% w/v vitamin C;
- 0.1% propylparaben; and
- 0.1% methylparaben.

Storage:

Once the protectant, stabilizers, antimicrobials, antioxidants, and alkalinizing agents are added and mixed into the liquid egg material, the liquid egg material is packaged in suitable storage containers.

The containers can be stored frozen, refrigerated or at room temperature. Storing the shelf-stable liquid egg material at room temperature is an advantage as storage costs are considerably less without the need for refrigeration. In addition, the ability to store the liquid egg material at room temperature renders it useful for farms that do not have refrigeration readily available, as found in developing countries. While the liquid egg material of the present invention can be stored for extended periods at room temperature, refrigeration or freezing of the liquid egg material can extend the shelf life even further.

Preferred Recipe of Liquid Egg Material and Method of Making Same:

Whole eggs are cracked open manually or using automated methods into a container at room temperature. The yolks can be separated into a separate container and processed as a yolk-only material, if desired.

Glycerol, sodium chloride, potassium sorbate, vitamin E, vitamin C, propylparaben, and methylparaben are added at room temperature to the liquid egg material and mixed. These ingredients can be added in any order as long as thorough mixing is achieved. In a preferred version, glycerol is added first, followed by sodium chloride, potassium sorbate, vitamin E, vitamin C, propylparaben, and methylparaben to ensure thorough dissolution of each ingredient. Thorough mixing is carried out to dissolve solid ingredients using a blender or other automated mixing equipment known to the art. The mixed liquid egg material is packaged into light-proof containers and stored at a desired storage temperature.

Use of Invention:

The liquid egg material of the present invention can be used to provide passive immunity to any animal and is particularly useful with livestock. The liquid egg material of the present invention is suitable for use on all mammals including but not limited to the bovine species, ovine species, canine species, feline species, caprine species, swine species and equine species, all avian species including chickens and turkeys, all reptile species, all fish species, and all invertebrate species. The preferred methods of administering the liquid egg material to the animal includes oral administration, although other methods such as parenteral administration are also acceptable.

Use of the liquid egg material of the present invention to provide passive immunity to livestock is achieved by pouring the invention into watering systems or by directly drenching animals. The liquid egg material may be given directly to the animal; mixed into dry feed; mixed into liquid feed; or mixed into water and then given to the animal. Non-limiting examples of preferred administrations include the following:

For poultry, 8 ounces of the liquid egg material is mixed with 1 gallon of water to form a stock solution. The stock solution can then be metered into drinking water at the rate of 1 ounce of stock solution per gallon of drinking water.

For swine, a stock solution can be prepared and metered at the rate of 1 gallon stock solution per 128 gallons of water through a medicator. A proposed stock solution formula is prepared according to the following recommendations:

Sows and Boars: 8 ounces of the liquid egg material to 1 gallon of water

Nursery: 16 ounces of the liquid egg material to 1 gallon of water

Growers and Finishers: 8 ounces of the liquid egg material to 1 gallon of water

For the bovine species, it is preferred to add 4 ml of the liquid egg material of the present invention to milk or milk replacer once per calf daily for 7 days, followed by 2 ml per day until weaning. This is accomplished by making a stock solution of formula of the present invention and metering to calves at the rate of 1 gallon of stock solution per 128 gallons of milk or milk replacer once daily. A preferred concentration follows. For the first 7 days after birth, water is added to 32 ounces of the liquid egg material of the invention until the volume makes up 1 gallon of stock solution. From day 8 until weaning, water is added to 16 ounces of the liquid egg material of the invention until the volume makes up 1 gallon of the stock solution.

The liquid egg material of the present invention provides considerable ease of use to the end user to provide specific IgY passive immunity.

Unless explicitly indicated otherwise, all concentrations described herein indicate the final concentration in the liquid egg material. References to percent weight per volume (w/v) or volume per volume (v/v) indicates weight or volume, respectively, of the added component per final volume of liquid egg material.

The ingredients and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

The methods, compounds, and compositions of the present invention can comprise, consist of, or consist essentially of the steps, ingredients, and limitations described herein, as well as any additional or optional steps, ingredients, or limitations described herein or otherwise useful in the art.

EXAMPLES

The following Examples demonstrate how the present invention has been practiced, but should not be construed as limiting.

Example 1

Egg-laying chickens were hyperimmunized with a commercially available coronavirus vaccine. After a suitable time to allow specific IgY titer to coronavirus to increase, the eggs were collected and cracked open to obtain the entire liquid egg contents of the whites and yolk. The resultant volume of the whole egg-derived liquid egg material was measured. Glycerol was added and mixed into the liquid egg material to a final concentration of 20% v/v. Sodium chloride was then mixed into the liquid egg material to a final concentration of 10% w/v, along with potassium sorbate at 0.1% w/v, vitamin C at 0.1% w/v, vitamin E at 0.1% w/v, sodium carbonate at 2% w/v, and soybean trypsin inhibitor at 0.1% w/v. This liquid egg material was then subjected to analysis for IgY to specific coronavirus by Enzyme Linked Immuno Assay (ELISA) to generate a baseline IgY titer concentration.

Aliquots of the liquid egg material were stored frozen at −20° C., refrigerated at 4° C., or at room temperature at 22° C., 37° C. or 55° C. Periodic sampling occurred weekly over the course of 6 weeks. and the samples were analyzed by ELISA for IgY titer concentrations. No changes were observed in the IgY titer concentrations. Accelerated stability studies using Arrhenius plot calculations indicate the stability of the specific IgY for coronavirus is greater than 1 year at room temperature under the conditions used. The matrix of the whole egg-derived egg material remained liquid, and no microbial growth occurred at any temperature used. The frozen storage conditions showed no changes in IgY titer upon thawing, indicating stability of the IgY in the liquid egg material of the present invention even when frozen and then thawed.

Example 2

Egg-laying chickens were hyperimmunized with a commercially available coronavirus vaccine. After a suitable time to allow specific IgY titer to coronavirus to increase, the eggs were collected and cracked open to obtain just the yolk. The resultant volume of the yolk-derived liquid egg material was measured. Glycerol was added and mixed into the liquid egg material to a final concentration of 20% v/v. Sodium chloride was then mixed into the liquid egg material to a final concentration of 10% w/v, along with potassium sorbate at 0.1% w/v, vitamin C at 0.1% w/v, vitamin E at 0.1% w/v, sodium carbonate at 2% w/v, and soybean trypsin inhibitor at 0.1% w/v. The liquid egg material was then subjected to analysis for IgY to specific coronavirus by Enzyme Linked Immuno Assay (ELISA) to generate a baseline IgY titer concentration.

Aliquots of this final liquid matrix were stored frozen at −20° C., refrigerated at 4° C., or at room temperature at 22° C., 37° C., or 55° C. Periodic sampling occurred weekly over the course of 6 weeks, and the samples were analyzed by ELISA for IgY titer concentrations. No changes were observed in the IgY titer concentrations. Accelerated stability studies using Arrhenius plot calculations indicate the stability of the specific IgY for coronavirus is greater than 1 year under the conditions used. The matrix of the yolk-derived egg material remained liquid, and no microbial growth occurred at all temperatures. The frozen storage conditions showed no changes in IgY titer upon thawing, indicating stability of the IgY in the liquid egg material of the present invention even when frozen and then thawed.

The present invention is not intended to be limited to the foregoing examples, but to encompass all such modifications and variations as come within the scope of the appended claims. It is understood that the invention is not confined to the particular construction and arrangement of parts herein illustrated and described, but embraces such modified forms thereof as come within the scope of the claims following the cited references.

BIBLIOGRAPHY

Chang H. M., Ou-Yang R. F., Chen Y. T. & Chen C. C., 1999. Productivity and some properties of immunoglobulin specific against Streptococcus mutans serotype C in chicken egg yolk (IgY). J. Agric. Food Chem., 47, 61-66.

Chansarkar N. L., 1998. Studies on structural stability of hen's egg yolk immunoglobulin (IgY). *PhD Thesis*: University of British Columbia (Canada).

Hatta H. et al., 1997. Passive immunization against dental plaque formation in humans: effect of mouth rinse containing egg yolk antibodies (IgY) specific to Streptococcus mutans. Caries *Res.*, 31, 268-274.

Kassaify Z. G., Li E.& Mine Y., 2005. Identification of anti-adhesive fraction(s) in non-immunized egg yolk powder: in vitro study. J. Agric. Food Chem., 53, 4607-4614.

Klemperer F., 1893. Ueber natürliche Immunität und ihre Verwertung für die Immunisierungstherapie. Arch. Exp. Pathol. Pharmakol., 31, 356-382.

J. D. Quigley, K. R. Martin, H. H. Dowlen, and K. C. Lamar. 1995. Addition of Soybean Trypsin Inhibitor to Bovine Colostrum: Effects on Serum Immunoglobulin Concentrations In Jersey Calves. J Dairy Sci 78:886-892.

Sugita-Konishi Y. et al., 2002. Inhibition of bacterial adhesion and Salmonella infection in BALB/c mice by sialyoligosaccharides and their derivatives from chicken egg yolk. *J. Agric. Food Chem.*, 50, 3607-3613.

U.S. Pat. No. 6,403,141. Method of obtaining long shelf life liquid egg products. Liot, M.

What is claimed is:

1. A shelf-stable liquid egg material, comprising:
    a liquid egg material enriched with an antibody at a hyper-immunized titer; and
    additional ingredients comprising:
        an antibody protectant;
        an antioxidant;
        an antimicrobial agent;
        a digestive enzyme inhibitor; and
        an alkalinizing agent,
    wherein the additional ingredients are present in concentrations effective to extend shelf life of the liquid egg material.

2. The liquid egg material of claim 1 wherein the liquid egg material comprises inner content of an egg that is selected from the group consisting of whole egg, egg yolk, and egg white.

3. The liquid egg material of claim 1 wherein the antibody protectant is selected from the group consisting of glycerol, propylene glycol, ethylene glycol, and combinations thereof.

4. The liquid egg material of claim 1 wherein the antibody protectant is present in the liquid egg material at a final concentration of from about 1% to about 60% v/v.

5. The liquid egg material of claim 1 wherein the antimicrobial agent is selected from the group consisting of sucrose, sodium chloride, potassium sorbate, methylparaben, propylparaben and an essential oil, wherein the essential oil is selected from the group consisting of oregano, garlic, thyme, rosewood, celery seed, frankincense, yiang yiang, cedarwood, lime, orange, petitgrain, bergamot, lemon, grapefruit, mandarin, myrrh, coriander, pumpkin, cypress, lemongrass, palmarosa, citronella, carrot seed, eucalyptus, fennel, wintergreen, juniper, French lavender, Tasmanian lavender, macadamia, tea tree, cajuput, niaouli, peppermint, spearmint, basil, evening primrose, marjoram, geranium, aniseed, bay, pine, black pepper, patchouli, apricot kernel, sweet almond, rosemary, sage, clary sage, sandalwood, clove, vetiver, and ginger oil.

6. The liquid egg material of claim 1 wherein the antimicrobial agent is present in the liquid egg material at a final concentration of from about 1% to about 60% w/v.

7. The liquid egg material of claim 1 wherein the antimicrobial agent comprises sucrose at a final concentration of from about 1% to about 60% w/v.

8. The liquid egg material of claim 1 wherein the antimicrobial agent comprises sodium chloride at a final concentration of from about 1% to about 30% w/v.

9. The liquid egg material of claim 1 wherein the antimicrobial agent comprises potassium sorbate at a final concentration of from about 0.01% w/v to about 0.1% w/v.

10. The liquid egg material of claim 1 wherein the antimicrobial agent comprises propylparaben and methylparaben, each at a final concentration of from about 0.01% w/v to about 0.1% w/v.

11. The liquid egg material of claim 1 wherein the antimicrobial agent comprises an essential oil at a final concentration of from about 0.0001% v/v to about 5% v/v.

12. The liquid egg material of claim 1 wherein the antioxidant is selected from the group consisting of tocopherol, gallic acid ester, dibutyl hydroxy toluene (BHT), butyl hydroxy anisol (BHA), ascorbic acid (vitamin C), vitamin E, and combinations thereof.

13. The liquid egg material of claim 1 wherein the antioxidant is present in the liquid egg material at a final concentration of from about 0.01% w/v to about 5% w/v.

14. The liquid egg material of claim 1 wherein the antioxidant is vitamin E or vitamin C and is present in the liquid egg material at a final concentration of from about 0.01% w/v to about 5% w/v.

15. The liquid egg material of claim 1 wherein the antioxidant is dibutyl hydroxyl toluene (BHT) or butyl hydroxyl anisol (BHA) and is present it the liquid egg material at a concentration of from about 0.01% w/v to about 0.02% w/v.

16. The liquid egg material of claim 1 wherein the digestive enzyme inhibitor is selected from the group consisting of soybean trypsin inhibitor, a chymotrypsin inhibitor, a carboxypeptidase inhibitor, a papain inhibitor, and a pepsin inhibitor.

17. The liquid egg material of claim 1 wherein the digestive enzyme inhibitor is soybean trypsin inhibitor.

18. The liquid egg material of claim 1 wherein the digestive enzyme inhibitor is present in the liquid egg material at a final concentration from about 0.0001% w/v to about 0.1% w/v.

19. The liquid egg material of claim 1 wherein the alkalinizing agent is selected from the group consisting of sodium carbonate, sodium bicarbonate, calcium carbonate, magnesium carbonate, and combinations thereof.

20. The liquid egg material of claim 1 wherein the alkalinizing agent is present in the liquid egg material at a concentration of from about 2.0% w/v to about 10% w/v.

21. The liquid egg material of claim 1 wherein:
the antimicrobial agent comprises about 10% w/v sodium chloride, about 0.1% w/v potassium sorbate, about 0.1% w/v propylparaben, and about 0.1% w/v methylparaben;
the antibody protectant comprises about 20% v/v glycerol; and
the antioxidant comprises about 0.1% w/v vitamin E and about 0.1% w/v vitamin C.

22. The liquid egg material of claim 1 wherein the antibody comprises an IgY antibody.

23. A method of making the shelf-stable liquid egg material as described in claim 1, comprising:
inducing an immune response in an egg-producing animal with at least one antigen to produce an antibody at a hyperimmunized titer;
collecting an egg from the egg-producing animal following induction of the immune response;
processing inner content of the egg to obtain a liquid egg material; and
adding to the liquid egg material in concentrations effective to extend shelf life of the liquid egg material:
an antibody protectant;
an antioxidant;
an antimicrobial agent;
a digestive enzyme inhibitor; and
an alkalinizing agent.

24. A method of using a shelf-stable liquid egg material as described in claim 1, comprising administering the liquid egg material to an animal to provide passive immunity to the animal.

25. The method of claim 24 further comprising, prior to the administering, storing the liquid egg material for a period of at least six months at room temperature.

* * * * *